(12) United States Patent
Qiao et al.

(10) Patent No.: US 10,788,473 B2
(45) Date of Patent: Sep. 29, 2020

(54) COMPUTING SYSTEM FOR DETECTING TOTAL PHOSPHORUS IN EFFLUENT USING DATA DRIVEN A²/O PROCESS

(71) Applicant: Beijing University of Technology, Beijing (CN)

(72) Inventors: Junfei Qiao, Beijing (CN); Ying Hou, Beijing (CN); Honggui Han, Beijing (CN)

(73) Assignee: Beijing University of Technology, Beijing (CN)

( * ) Notice: Subject to any disclaimer, the term of this patent is extended or adjusted under 35 U.S.C. 154(b) by 0 days.

(21) Appl. No.: 15/206,702

(22) Filed: Jul. 11, 2016

(65) Prior Publication Data
US 2017/0299565 A1 Oct. 19, 2017

(30) Foreign Application Priority Data
Apr. 15, 2016 (CN) .......................... 2016 1 0237451

(51) Int. Cl.
*G01N 33/18* (2006.01)
(52) U.S. Cl.
CPC ........... *G01N 33/18* (2013.01); *G01N 33/182* (2013.01)

(58) Field of Classification Search
CPC ...................................................... G01N 33/18
USPC ............................................................ 702/25
See application file for complete search history.

(56) References Cited

U.S. PATENT DOCUMENTS

| 5,641,966 A | * | 6/1997 | Karlberg | ................ G01N 21/31 250/373 |
| 2015/0034553 A1 | * | 2/2015 | Kumar | ................... C02F 3/006 210/610 |

FOREIGN PATENT DOCUMENTS

JP WO 2014142152 A1 * 9/2014 ........... G05B 23/024

* cited by examiner

*Primary Examiner* — Ricky Ngon
(74) *Attorney, Agent, or Firm* — Zhihua Han (57) ABSTRACT

A computing system is designed for measuring the A²/O effluent total phosphorus based on data-driven method. Several related variables are obtained by analyzing the relationship between effluent total phosphorus and other process variables. In addition, a hardware platform is designed and built to further analysis sample information of each variable. Finally, the computing system for measuring total phosphorus in effluent is developed by combining the hardware and software as provided in implementations herein.

1 Claim, 7 Drawing Sheets

COMPUTING SYSTEM FOR DETECTING TOTAL PHOSPHORUS IN EFFLUENT USING DATA DRIVEN A²/O PROCESS

CROSS REFERENCE TO RELATED DISCLOSURE APPLICATIONS

This application claims priority to Chinese Disclosure Application No. 201610237451.6, filed on Apr. 15, 2016, entitled "A Computing System for A²/O Effluent Total Phosphorus Based on Data-driven Method," which is hereby incorporated by reference in its entirety.

TECHNICAL FIELD

This disclosure relates to a process of monitoring variables online in wastewater treatment process (WWTP). In this disclosure, a computing system, based on data-driven method, is designed for effluent total phosphorus (ETP) of urban A²/O WWTP. Five categories of process variables, closely related to ETP, are initially introduced in this disclosure. Moreover, the specific sample location of each variable is then clarified. Finally, the intelligent computing system, through the integration of hardware, software, communication path and the embedded intelligent computing technology, has been developed for the online ETP measurement.

BACKGROUND

In the last century, rapid urbanization and industrialization processes led to serious environmental pollution and resource shortages. And lockage of freshwater resources has been one of worldwide attentions. Moreover, Chinese population problem and rapid industrialization make an increasing demand for fresh water resources. Environmental pollution problems of water resources are then serious and threat the social life and national long-term development. In response, research has been undertaken that led to the development of wastewater treatment technologies. Therefore, wastewater treatment facilities have been built, and positively promote the wastewater treatment capability of urban and industrial scenes. Based on the statistic results, 6031 WWTPs have been built in China by the end of 2014, and more than 1.8 hundred million of wastewater can be treated daily.

For a long time, since overload of ETP in rivers and lakes leads to eutrophication, abnormal growth of plants and serious damage to the ecological environment, ETP has been an important factor of effluent water quality standards in WWTP. Thereby, many countries have been set the ETP concentrations as a key effluent water quality factor in WWTP. However, in China, nearly 50% urban wastewater treatment plants cannot meet the national phosphorus emission standard. The main reason is that the ETP concentration cannot be obtained online. Therefore, the operation of WWTP cannot be adjusted online. Recently, the main method to measure ETP concentrations is the manual sampling method combining with chemical experiments. Although chemical methods can ensure high measurement accuracy, the complicated operation is very time-consuming (more than 1 hour), which cannot meet the increasing real-time requirements, and is easy to cause the second pollution. Recently, the rise of online instruments can realize the automatic collection and detection of wastewater samples. The time of measuring TP can be dramatically decreased (15 to 30 minutes) while accidental errors caused by manual operation can be avoided. However, these online instruments are based on a chemical mechanism. The purchase and maintenance costs of these online instrument are very high. A large number of wastewater treatment plants cannot afford these online instruments. Therefore, how to measure ETP with an accurate, reliable and economic way is still an open problem. And it is urgent to develop a novel technology to solve this problem.

As provided herein, the disclosure includes a usage of computing measurement techniques based on a neural network. Implementations of the disclosure can detect ETP online and with accurate performance, while the cost is affordable for wastewater treatment plants. However, research on detecting ETP in WWTP has not yet formed a complete system, and there is no available ETP detection system based on intelligent techniques. Therefore, the objective of this disclosure is to develop a computing system for estimating ETP concentrations in real time with high accuracy.

SUMMARY

Figure 1:
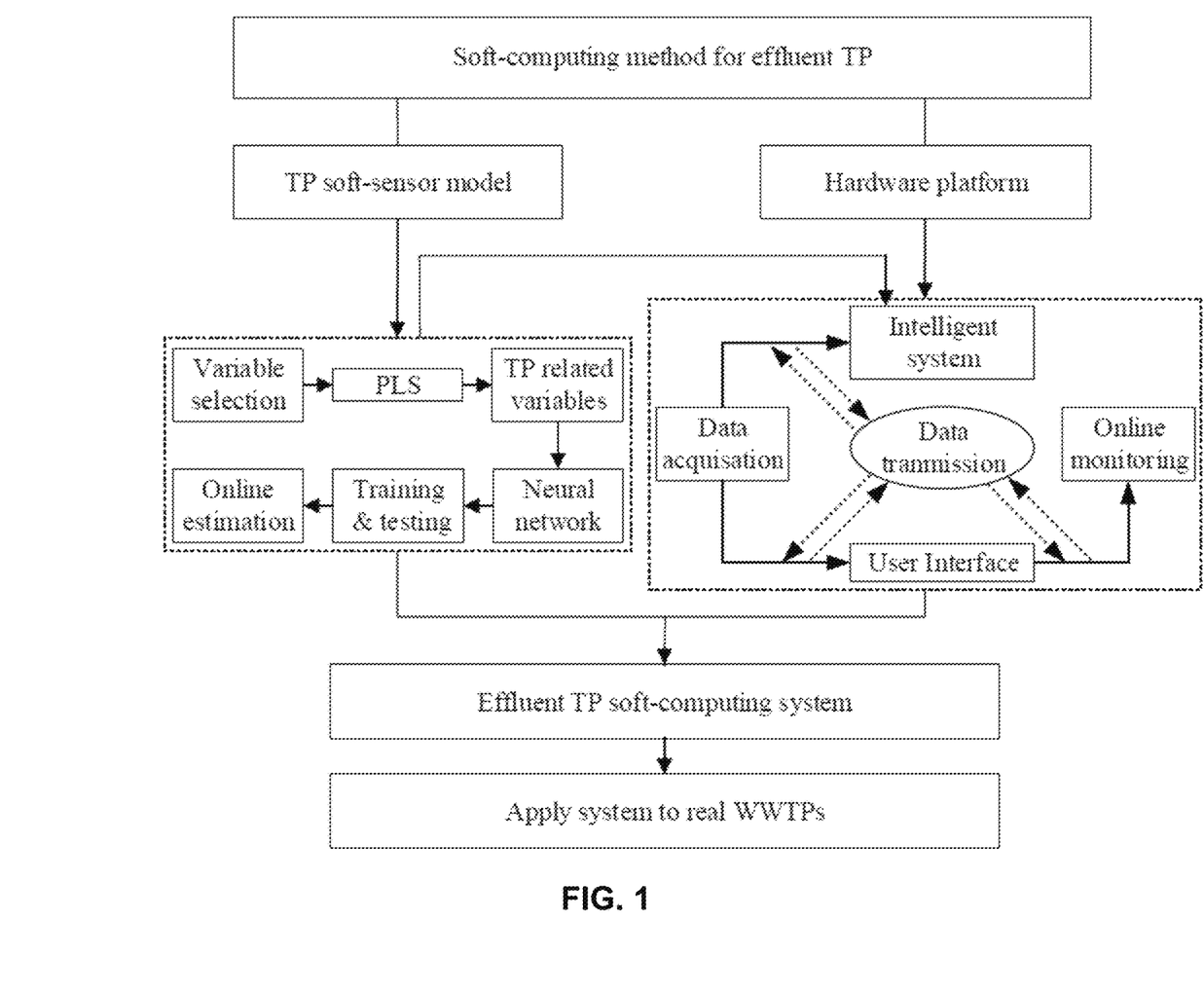
FIG. 1 shows a diagram of ETP computing system in accordance with implementations of the disclosure.

A data-driven computing system is developed for ETP in this disclosure. For this computing system, a hardware platform of ETP is introduced, while the communication path between hardware and software is also developed. Moreover, the ETP relevant process variables and their measurement position is decided, and real-time detecting technologies have been embedded into the ETP intelligent detection system. For this disclosure, the characteristic of ETP computing system is shown in FIG. 1, and the steps are as follow.

For ensuring the efficiency of ETP computing system, an intelligent method is proposed to build an intelligent model of ETP to overcome the challenge of WWTP with big-data. Specifically, dynamic characteristics of ETP are analyzed based on the dynamics of WWTP. In addition, the process variables that are related to the ETP concentration closely is selected based on the data mining method. Then, an artificial neural network is used to build the computing model of ETP. In this disclosure, the dynamic characteristics of ETP are analyzed using the activated sludge model No. 1 (ASM1) and the benchmark simulation model No. 1 (BSM1). Moreover, partial linear square (PLS) algorithm is used in this disclosure to select suitable process variables of ETP, since the PLS algorithm can extract the variables that carry most information as well as related to the output variable.

This disclosure adopts the following technical scheme and implementation steps:

Step 1:

Supposing the independent variable set as $X=[x_1, \ldots, x_\alpha]$, wherein $\alpha$ is the number of independent variables for n samples. Further, supposing the corresponding dependent variable vector as y. The data should be scandalized before using PLS algorithm to generate a functional relation between X and y. Moreover, the important components v and u are extracted from X and y respectively. Further, the PLS algorithm is used to build a linear model by decomposing X and y into bilinear terms:

$$X = VP^T + E = \sum_{i=1}^{\alpha} v_i p_i^T + E, \tag{1}$$

-continued $$y = UQ^T + F = \sum_{i=1}^{\alpha} u_i q_i^T + F, \quad (2)$$

wherein V and U are the score matrix of X and y, P and Q are the loading matrix of X and y, E and F are the residual matrix of X and y block, respectively. i=1, 2, . . . , α. Moreover, $v_i$, $p_i$, $u_i$ ⇌ $q_i$ are the corresponding vectors of V, P, U and Q.

Step 2:
Component $v_i$ and $u_i$ are then calculated by:

$$u_i = b_i v_i, \quad (3)$$

$$b_i = u_i^T v_i / v_i^T v_i, \quad (4)$$

wherein $b_i$ is the regression coefficient, the vector of the regression coefficients is $b=[b_1, b_2, \ldots, b_\alpha]^T$. α is the number of independent variables.

Step 3:
The predictors for the output variable can be selected as:

$$R_{select} = \frac{\|b_{select}\|}{\|b\|}, \quad (5)$$

wherein $b_{select}$ is the vector of the regression coefficients of the selected variables, $R_{select}$ is the importance of the selected variables and will be determined by leave-one-out method. ‖•‖ is norm operation. In this disclosure, $R_{select}$ is set as 0.85.

The main components of hardware platform include the pre-treatment tank, the first settler, the anaerobic tank, the anoxic tank, the oxic tank and the second settler. Different measuring devices are placed in the platform to measure the total suspended solid (TSS), pH (include temperature), the dissolved oxygen (DO) in the oxic tank and the oxidation-reduction potential (ORP) in the anaerobic tank online in this disclosure. The obtained data are stored in the devices at first, then the computing system of effluent total phosphorus can transfer the data to the intelligent model in real time. Finally, the value of effluent total phosphorus concentration can be estimated online.

BRIEF DESCRIPTION OF THE DRAWINGS

The detailed description is described with reference to the accompanying figures.

DETAILED DESCRIPTION

The PLS algorithm is used to select the related variables of ETP. The selecting results are shown in table 1.

TABLE 1

The information of process variables in WWTP

| Name | Unit | Measuring method | Sample interval and location | Relation to ETP |
|---|---|---|---|---|
| pH | — | Online instrument | Seconds, effluent | Related |
| Temperature | °C. | Online instrument | Seconds, multiple | Related |
| DO | mg/L | Online instrument | Minutes, oxic | Related |
| $NH_4$—N | mg/L | Online instrument | Hours, effluent | Unrelated |
| $NO_3$—N | mg/L | Online instrument | Hours, effluent | Unrelated |
| ORP | mV | Online instrument | Hours, effluent | Related |
| TSS | mg/L | Online instrument | Hours, oxic tank | Related |
| MLSS | mg/L | Online instrument | Hours, anaerobic | Unrelated |
| COD | mg/L | Labor + labratory | Day, influent/effluent | Related |
| BOD | mg/L | Labor + labratory | 5 days, effluent | Related |
| TP | mg/L | Labor + labratory | Hours, influent | Related |

Figure 2:
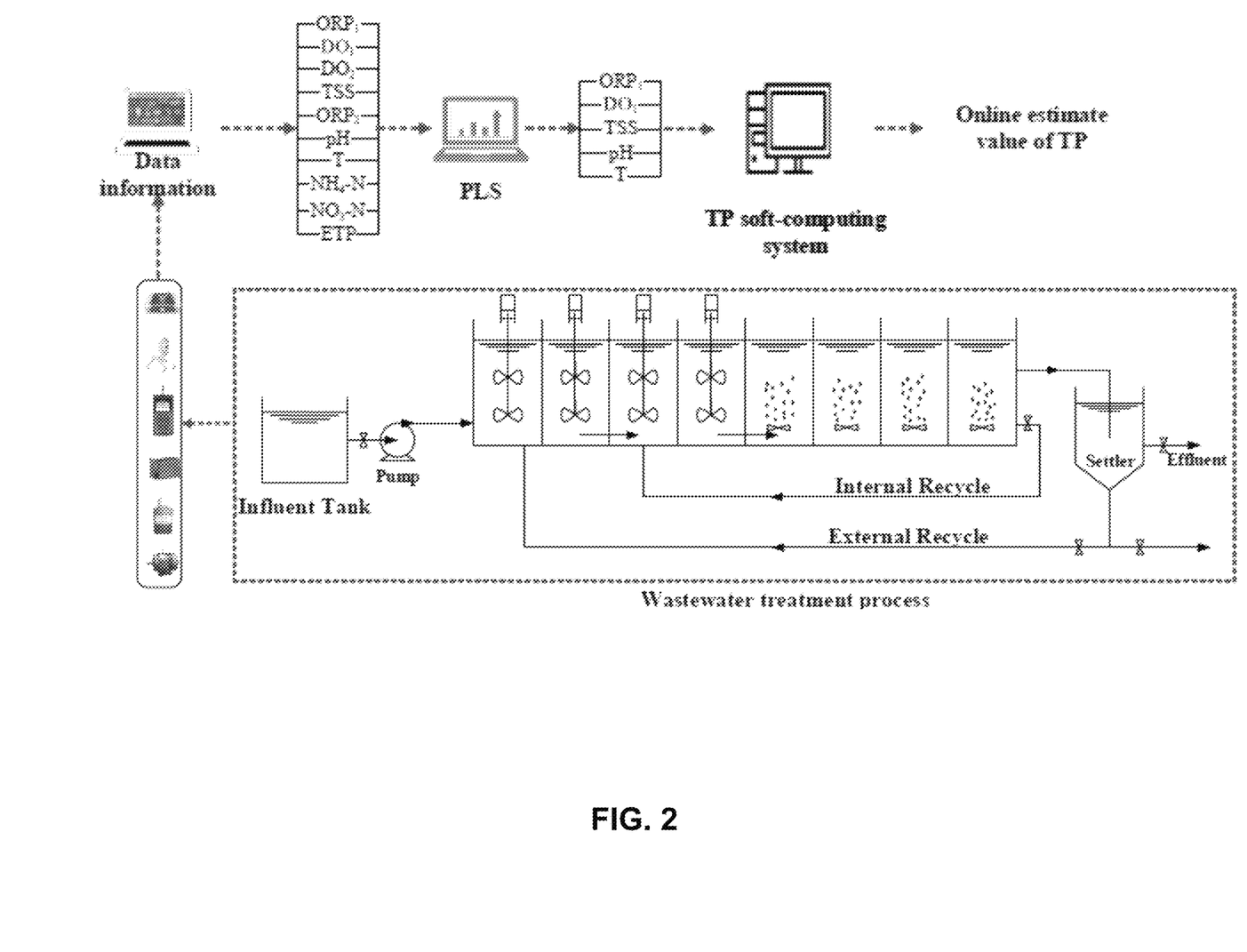
FIG. 2 shows a hardware platform and data transmission process of ETP computing system in accordance with implementations of the disclosure.

Due to limitation in the real WWTP, a measuring interval and sample location of each variable are determined by real operations of WWTP. However, concentrations of some parameters (such as DO, ORP, etc.) vary from different sample locations; this situation can make negative impact on the accuracy of the data analysis. Therefore, to ensure the accuracy, a hardware platform for ETP computing system is built, and the diagram of the platform is shown in FIG. 2. Then, the parameters in table 1 are analyzed to determine the useful variables. ① The concentrations of pH and temperature are steady in the whole process, only effluent tank is set as a sample location. ② Based on the preliminary results, $NH_4$—N and $NO_3$—N are only measured in the effluent tank to verify the relationship between them and ETP. ③ The instruments for COD and BOD are very expensive. Thus, there are no instruments of COD and BOD. ④ The concentrations of DO and ORP vary from different sample locations, and the relationship between DO, ORP and ETP need to be future analyzed.

Figure 3:
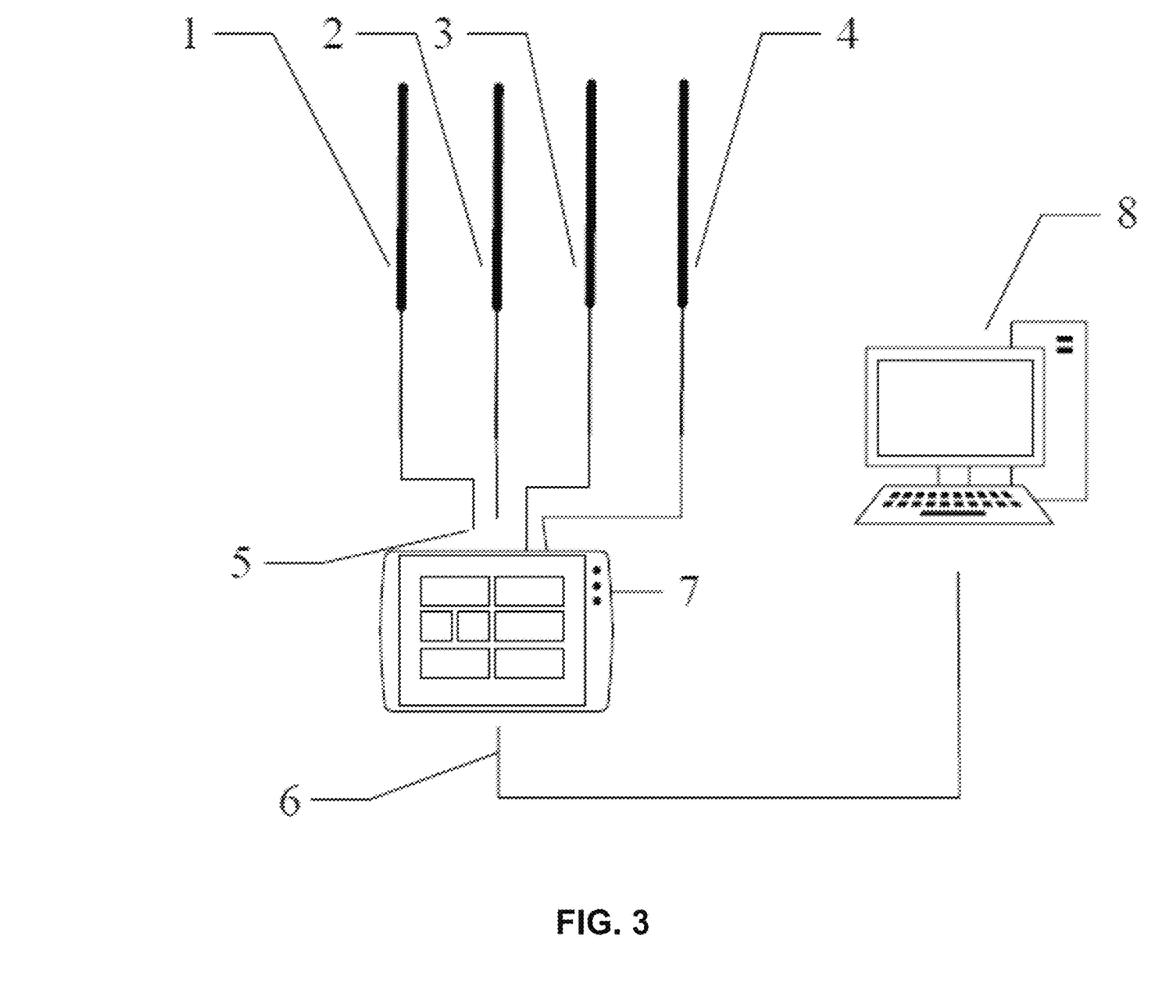
FIG. 3 shows a connection of system and online instruments of ETP computing system in accordance with implementations of the disclosure.

The main components of hardware platform include the pre-treatment tank, the first settler, the anaerobic tank, the anoxic tank, the oxic tank and the second settler. Different instruments are placed in the platform to obtain the process variables that related to ETP. In general, the online measuring instruments of TSS, pH (include temperature), DO, ORP, $NH_4$—N and $NO_3$—N are used. The connection details of the system and the online instruments are shown in FIG. 3: parts 1-4 is the ports of different variables, part 5 is the connecting port between the ports and the sample devices, part 6 is the transport line between the sample devices and PC, and part 7 is the sample device (WTW 3430 in this disclosure). Moreover, part 8 is the PC system with the ETP computing system.

The data, collected by the instruments, may be pre-treated to eliminate random errors. Moreover, these data may be transferred from the instruments to the PC system through the OPC sever. Then, through a data deliver model developed in this disclosure, the data could be transferred to the ETP computing system in real time. To maintain the dynamic characteristics of the system, the recording time (not sample time) of every variable are set as the same.

Based on the above analysis, temperature, TSS, pH, DO in the oxic tank and ORP in the anaerobic tank are selected as the related variables of ETP. The sample information of each variable is shown in table 2.

TABLE 2

The sample information of each ETP related variable

| Name | Unit | Sample interval and location | Relation to ETP |
|---|---|---|---|
| pH | — | Seconds, effluent | Related |
| Temperature | °C. | Seconds, multiple | Related |
| DO | mg/L | Minutes, oxic | Related |
| ORP | mV | Hours, effluent | Related |
| TSS | mg/L | Hours, oxic tank | Related |

After building the hardware platform and verifying the efficiency of the computing model for ETP, the computing system of ETP is then developed in this disclosure. Component technology is used here to package each function module (data acquisition, data transfer, TP estimate, etc.) and to combine the hardware platform with the software, thereby integrating the ETP computing system.

Figure 4:
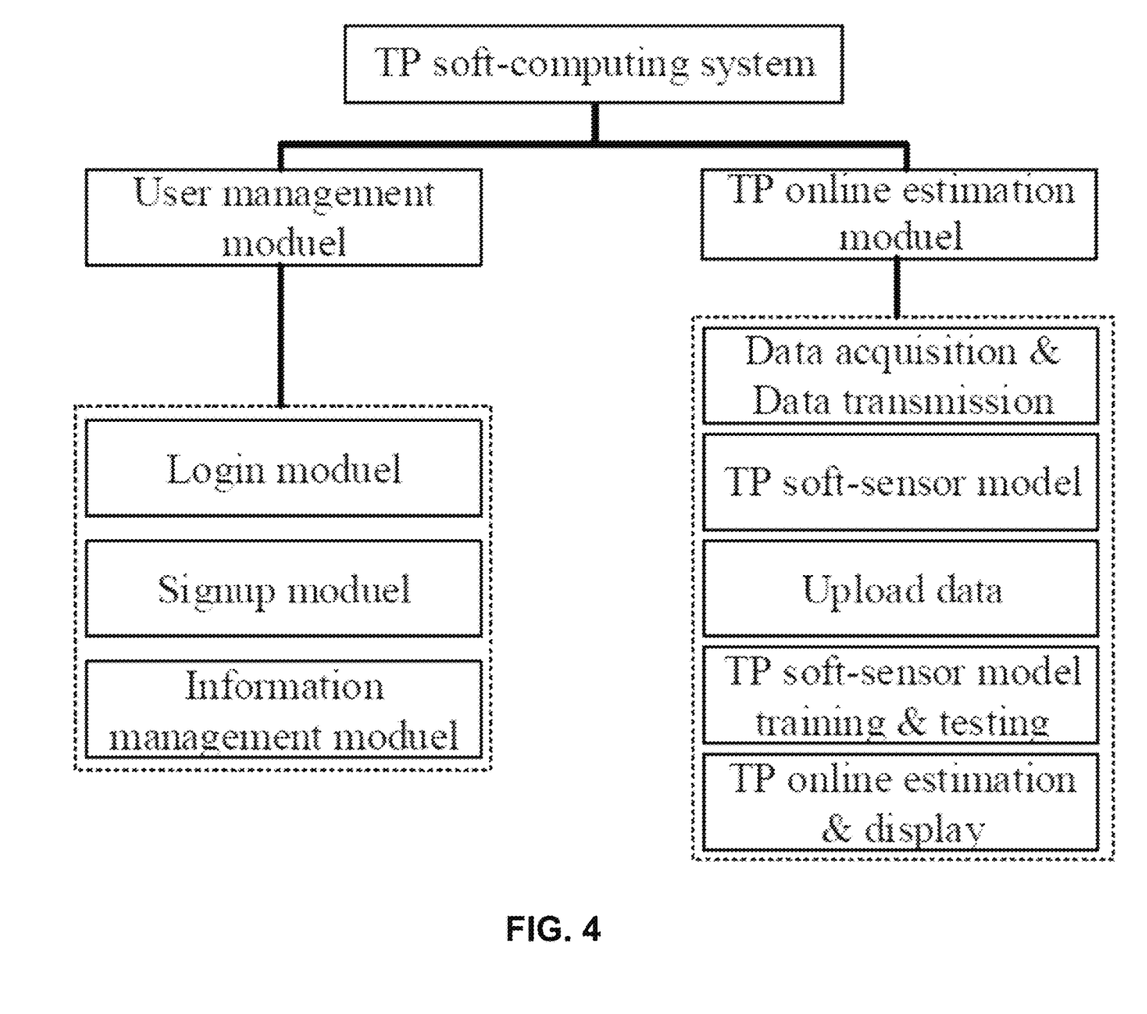
FIG. 4 shows a software structure of ETP computing system in accordance with implementations of the disclosure.

A data transmission mechanism is proposed in this disclosure to make the computing system of ETP with the capable of various operations such as data acquisition, data transmission, data saving and ETP estimation. The diagram of ETP computing system is shown as FIG. 4. The main functions of this system are as follows: ① obtaining the data of the related process variables, ② training and testing of ETP computing model off-line, and ③ estimating and displaying the concentration value of ETP online in real time.

Figure 5:
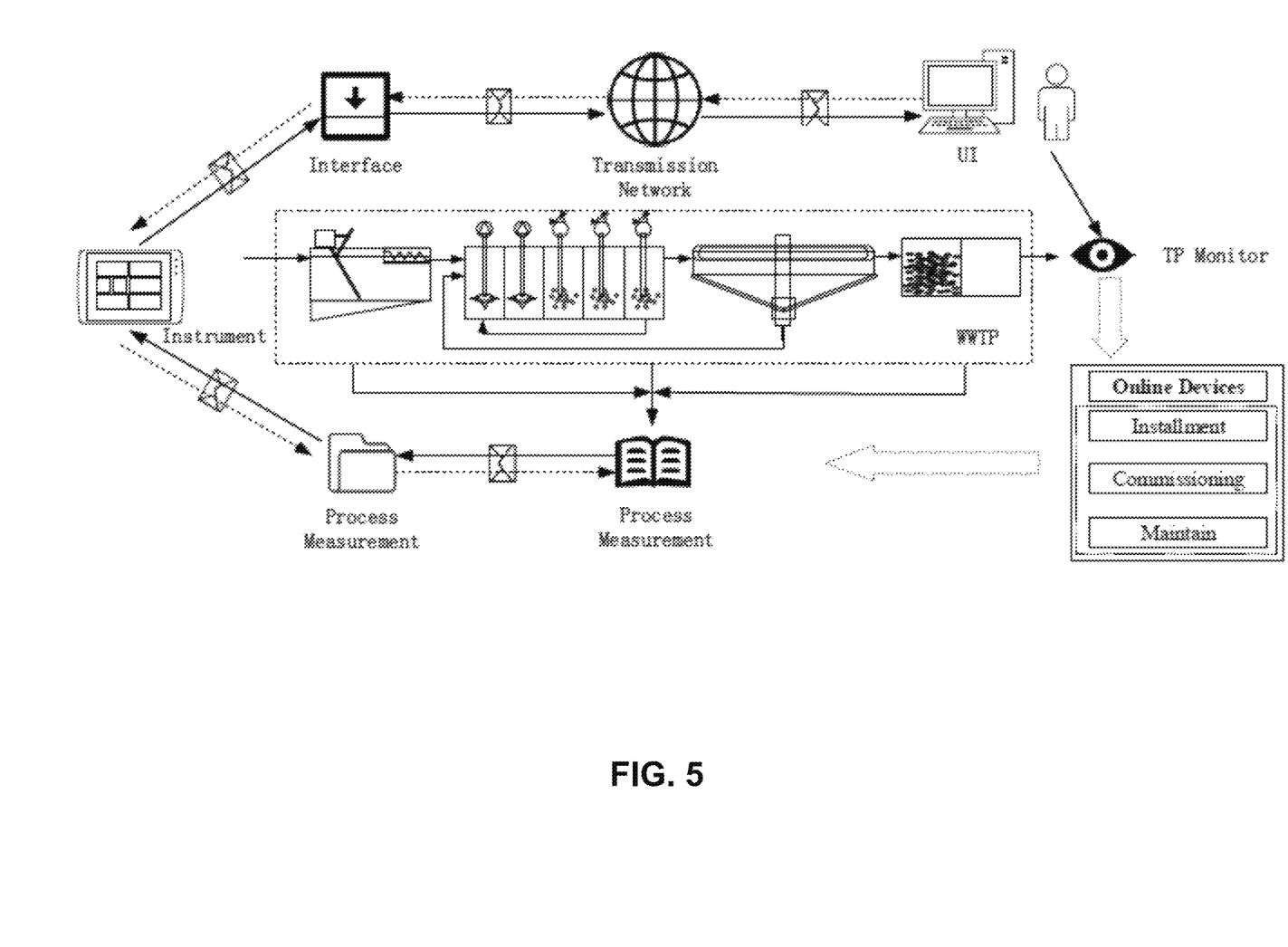
FIG. 5 shows an impletion diagram of ETP predicting method in accordance with implementations of the disclosure.

When the system is used in a real WWTP, the data information of related variables may be obtained in the first place and stored in the instruments. Then, the data may be transferred to ETP computing system to estimate the concentration of ETP online. Moreover, the system could package each function module based on the environment of WWTP, and give the suggestions to detect process error. The whole working flow of ETP computing system is shown as FIG. 5.

Compared with the conditional ETP estimation method in WWTP, the innovation of this disclosure are as follows.

(1) Selecting five related variables of ETP.

In order to detect the ETP concentration online with acceptable accuracy, a method to select the related variables of ETP has been proposed in this disclosure. Five related process variables are presented and the specific sample location of each variable has been cleared.

(2) Synchronizing the time-serous of each variable.

As to those related variables that cannot be access in real time, the online instruments have been installed to ensure the integrity and accuracy of data information. Moreover, the data information is transmitted to the host computer through a coordination communication standard.

(3) Integrating the hardware and software platform, and packaging of data acquisition, data transmission, data storage, and ETP intelligent detection modules into a whole system.

(1) Process to Develop the Intelligent Computing Method for ETP

When using the PLS algorithm to analysis the related variables of ETP, a real WWTP is designed along with the hardware platform in this disclosure. The daily treatment is about 20 m$^3$, the influent wastewater is the same as a real WWTP and the process is A$^2$/O.

Through the instruments that installed in the A$^2$/O process, there are 9 categories variables that need to be collected to make a further analysis by using the PLS algorithm. The sample information of each variable is shown as table 3.

TABLE 3

The sample information of each available variable

| Name | Unit | Sample location | Sample instrument | Sample interval |
|---|---|---|---|---|
| ORP1 | mV | Last anaerobic tank | SensoLyt700IQ | |
| DO1 | mg/L | First oxic tank | TriOxmatic700IQ | |
| DO2 | mg/L | Last oxic tank | TriOxmatic700IQ | |
| TSS | g/L | Effluent | ViSolid700IQ | 5 min |
| ORP2 | mV | Effluent | SensoLyt700IQ | |
| pH | — | Effluent | SensoLyt700IQ | |
| Temperature | °C. | Effluent | SensoLyt700IQ | |
| NH$_4$—N | mg/L | Effluent | SensoLyt700IQ | |
| NO$_3$—N | mg/L | Effluent | SensoLyt700IQ | |
| Effluent TO | mg/L | Effluent | Hach PHosPHaxSigma | 15 min |

② Pre-treating the data and remove abnormal data to avoid negative impact on data analyzing. The collected data is shown in table 4.

TABLE 4

Available data samples

| No. | ORP$_1$ (mV) | DO$_1$ (mg/L) | DO$_2$ (mg/L) | TSS (g/L) | ORP$_1$ (mV) | PH | 温度 (°C.) | NH$_4$—N (mg/L) | NO$_3$—N (mg/L) | ETP (mg/L) |
|---|---|---|---|---|---|---|---|---|---|---|
| 1 | −437.1090 | 0.0470 | 8.5276 | 2.7725 | −5.2556 | 7.9068 | 26.9763 | 3.3971 | 12.0590 | 2.9740 |
| 2 | −437.7500 | 0.0494 | 8.6109 | 2.7709 | −5.9606 | 7.9069 | 26.9423 | 3.4023 | 12.1031 | 3.0020 |
| 3 | −412.0490 | 0.0656 | 8.6216 | 2.7997 | −5.7683 | 7.9024 | 26.9098 | 3.4096 | 12.1225 | 3.0260 |
| 4 | −410.2540 | 0.0529 | 8.5985 | 2.8186 | −5.5119 | 7.9015 | 26.8670 | 3.6459 | 12.1463 | 2.9660 |
| 5 | −383.0790 | 0.0559 | 8.7150 | 2.8151 | −5.7042 | 7.9005 | 26.8065 | 3.5625 | 12.1459 | 2.9040 |
| 6 | −371.4140 | 0.0591 | 8.7993 | 2.7939 | −4.9992 | 7.9030 | 26.7445 | 3.6221 | 12.1471 | 2.9540 |
| 7 | −380.6440 | 0.0562 | 8.8818 | 2.8203 | −5.3838 | 7.9055 | 26.6664 | 3.5660 | 12.1501 | 3.1900 |
| 8 | −363.4030 | 0.0518 | 8.9319 | 2.8032 | −5.8324 | 7.9069 | 26.5899 | 3.8020 | 12.1604 | 3.0400 |
| 9 | −373.2090 | 0.0617 | 8.9262 | 2.7863 | −6.7938 | 7.9105 | 26.5355 | 3.7300 | 12.1438 | 2.7300 |
| ... | ... | ... | ... | ... | ... | ... | ... | ... | ... | ... |
| 201 | −315.9750 | 0.1978 | 9.3234 | 2.7758 | −18.3945 | 7.9194 | 26.5516 | 3.7517 | 12.1550 | 2.3760 |

TABLE 4-continued

Available data samples

| No. | ORP₁ (mV) | DO₁ (mg/L) | DO₂ (mg/L) | TSS (g/L) | ORP₁ (mV) | PH | 温度 (° C.) | NH₄—N (mg/L) | NO₃—N (mg/L) | ETP (mg/L) |
|---|---|---|---|---|---|---|---|---|---|---|
| 202 | −360.8390 | 0.1624 | 9.2071 | 2.8790 | −18.3945 | 7.9214 | 26.6076 | 3.8495 | 12.1974 | 2.1900 |
| 203 | −466.0780 | 0.1327 | 9.0418 | 2.8295 | −20.3814 | 7.9199 | 26.6723 | 3.7980 | 12.2427 | 2.2300 |
| 204 | −488.1900 | 0.0972 | 8.7215 | 2.7999 | −15.5103 | 7.9172 | 26.7917 | 3.7584 | 12.5022 | 2.1360 |
| 205 | −495.9450 | 0.0654 | 8.4146 | 2.7858 | −13.5876 | 7.9191 | 26.9349 | 3.7364 | 12.7774 | 2.4080 |
| 206 | −528.9530 | 0.0644 | 8.1310 | 2.8053 | −16.7281 | 7.9200 | 27.0784 | 3.7422 | 12.8863 | 2.3360 |
| 207 | −540.2970 | 0.0518 | 7.6449 | 2.8251 | −17.4331 | 7.9266 | 27.2087 | 3.7214 | 12.9956 | 2.1840 |
| 208 | −546.8350 | 0.0394 | 6.3535 | 2.7176 | −16.5358 | 7.9298 | 27.2933 | 3.6922 | 13.0879 | 2.5480 |
| 209 | −552.1540 | 0.0383 | 4.3447 | 2.8343 | −16.7922 | 7.9298 | 27.3334 | 3.5761 | 13.1319 | 2.2080 |
| ... | ... | ... | ... | ... | ... | ... | ... | ... | ... | ... |
| 401 | −556.8970 | 0.0428 | 1.5381 | 2.8151 | −28.2006 | 7.9087 | 27.2888 | 3.3048 | 13.2904 | 2.8100 |
| 402 | −556.0000 | 0.0411 | 1.3376 | 2.7431 | −35.7635 | 7.8985 | 27.2681 | 3.3195 | 13.2117 | 2.7500 |
| 403 | −553.4360 | 0.0370 | 1.3321 | 2.7666 | −43.9674 | 7.8907 | 27.2354 | 3.3754 | 13.1971 | 2.8280 |
| 404 | −551.9620 | 0.0361 | 1.4133 | 2.7787 | −51.5302 | 7.8818 | 27.1983 | 3.4170 | 13.1739 | 2.9440 |
| 405 | −551.0650 | 0.0361 | 1.7262 | 2.7748 | −57.1704 | 7.8718 | 27.1584 | 3.4273 | 13.0797 | 3.1680 |
| 406 | −549.9110 | 0.0467 | 1.7702 | 2.7823 | −63.0669 | 7.8641 | 27.0976 | 3.4585 | 13.0552 | 2.6980 |
| 407 | −552.6030 | 0.0378 | 1.8569 | 2.7807 | −71.0143 | 7.8586 | 27.0192 | 3.5679 | 12.9795 | 3.2380 |
| 408 | −554.5260 | 0.0417 | 1.9737 | 2.7998 | −76.8467 | 7.8520 | 26.9526 | 3.5697 | 13.9270 | 3.1300 |
| 409 | −556.3200 | 0.0510 | 2.4058 | 2.8015 | −82.4869 | 7.8465 | 26.8788 | 3.5634 | 13.8076 | 3.3240 |
| ... | ... | ... | ... | ... | ... | ... | ... | ... | ... | ... |
| 601 | −561.1910 | 0.0382 | 2.8000 | 2.7686 | −95.3694 | 7.8448 | 26.6723 | 3.6763 | 13.3865 | 2.8240 |
| 602 | −562.0240 | 0.0612 | 3.7553 | 2.8298 | −98.1895 | 7.8481 | 26.6606 | 3.8572 | 13.1718 | 2.5940 |
| 603 | −562.9220 | 0.0387 | 5.6210 | 2.7908 | −101.1380 | 7.8490 | 26.6708 | 3.8836 | 12.8775 | 2.4740 |
| 604 | −563.7550 | 0.0410 | 6.0155 | 2.7883 | −104.2140 | 7.8498 | 26.6679 | 3.8814 | 12.5341 | 2.2040 |
| 605 | −561.4480 | 0.0602 | 6.1138 | 2.7827 | −97.8049 | 7.8517 | 26.7136 | 3.9342 | 11.9977 | 2.3920 |
| 606 | −555.0380 | 0.0411 | 6.0398 | 2.7556 | −89.2806 | 7.8536 | 26.8153 | 3.7086 | 12.6127 | 2.3180 |
| 607 | −548.5010 | 0.0363 | 5.9100 | 2.7975 | −80.6923 | 7.8579 | 26.9290 | 3.6714 | 12.6540 | 2.6040 |
| 608 | −543.7580 | 0.0706 | 6.1211 | 2.8063 | −77.4876 | 7.8622 | 27.0384 | 3.5926 | 12.7766 | 2.2340 |
| 609 | −550.9370 | 0.0472 | 5.9030 | 2.8011 | −71.9757 | 7.8643 | 27.1494 | 3.8618 | 12.7819 | 2.5300 |
| ... | ... | ... | ... | ... | ... | ... | ... | ... | ... | ... |

Figure 6:
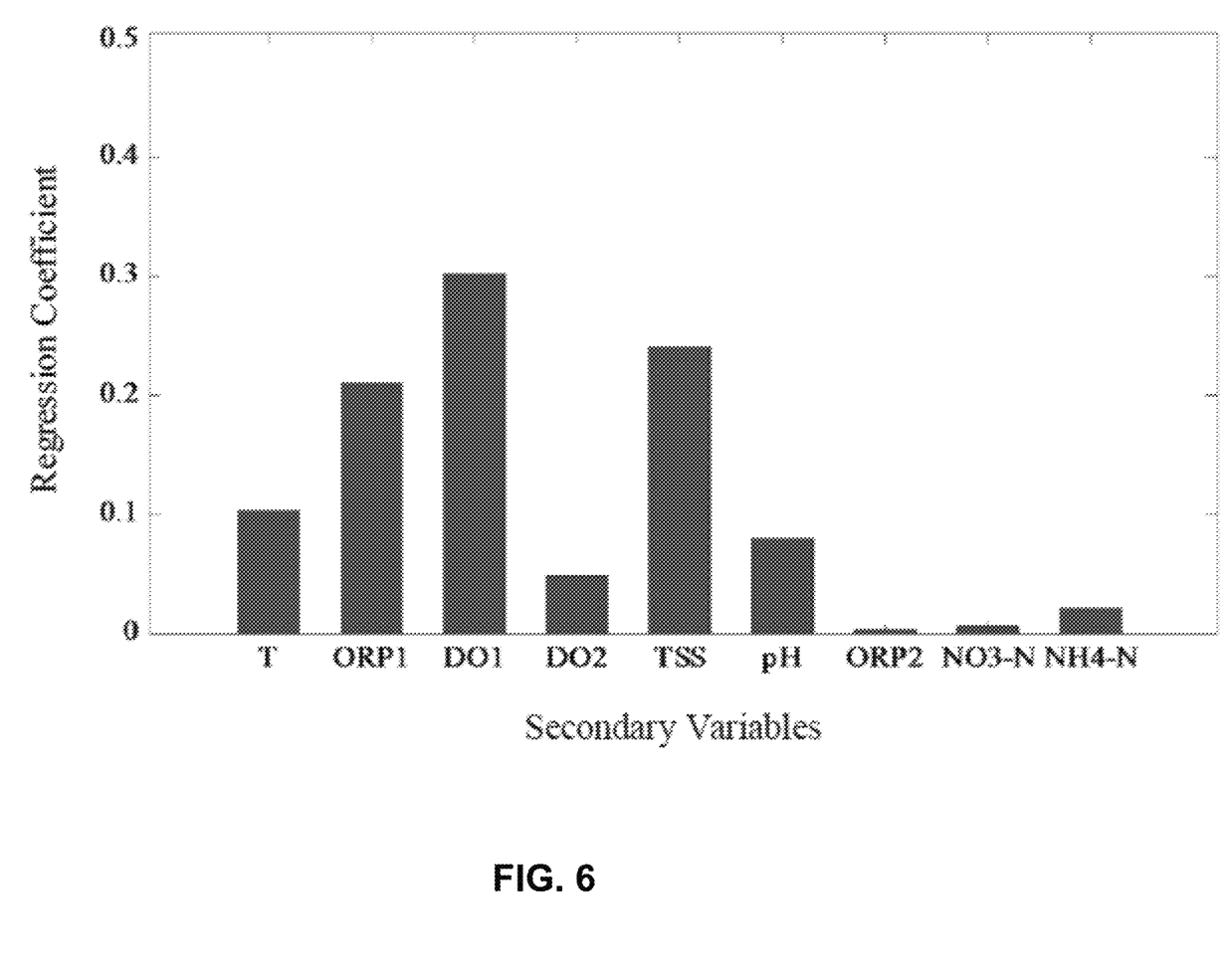
FIG. 6 shows selecting results of ETP related variables in accordance with implementations of the disclosure.
Figure 7:
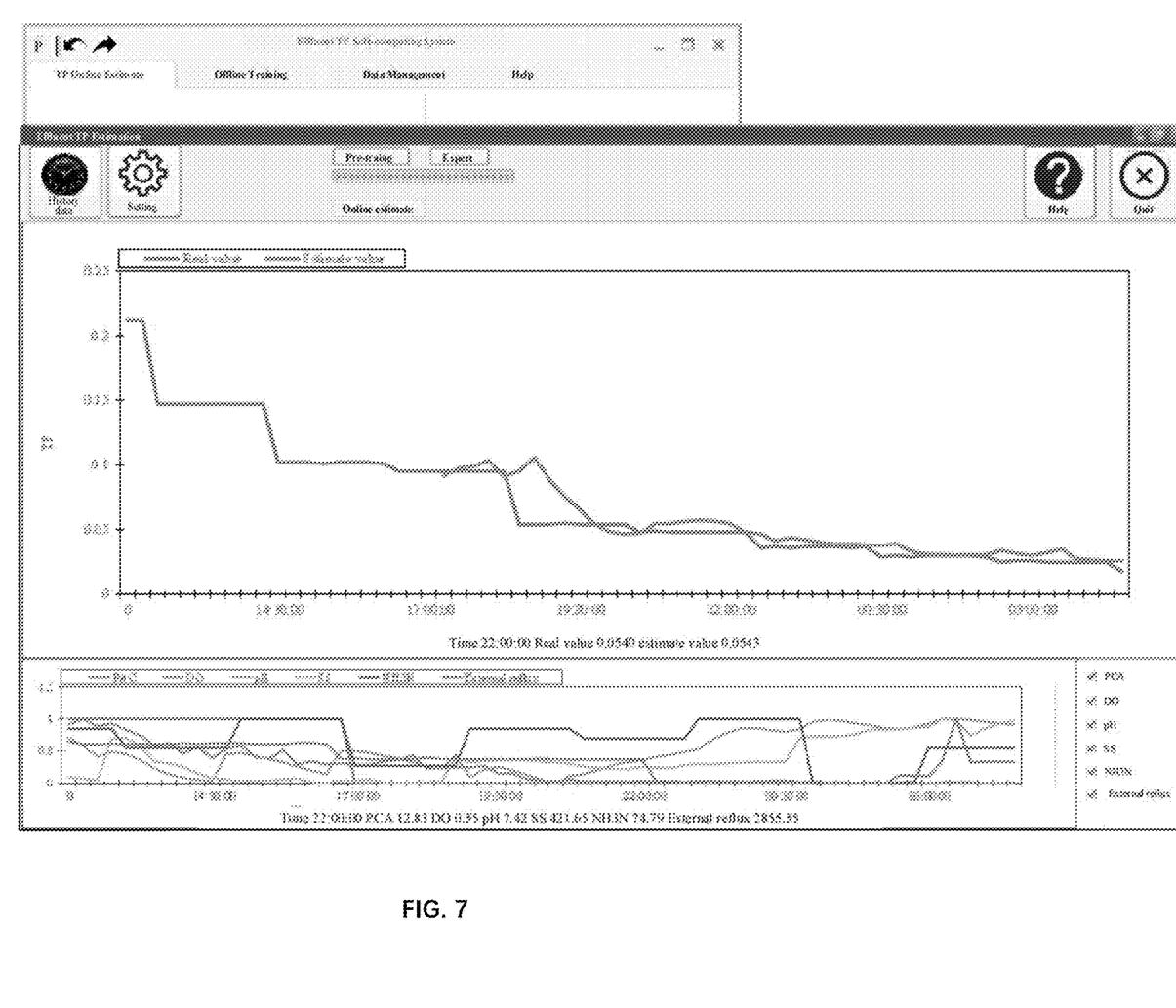
FIG. 7 shows application performance of ETP computing system in accordance with implementations of the disclosure.

(3) Using the PLS algorithm to perform analysis the data in table 4, and the result is shown in FIG. 6. After the above analysis, temperature, TSS, pH, DO in the oxic tank and ORP in the anaerobic tank are selected as the related variables of TP.

(2) Design of ETP Computing System and the Combination of Software and Hardware

Before developing the computing system of ETP, a hardware platform is developed in this disclosure to simulate the real WWTP and to offer the data information. Then, this data information may be transferred to the computing system of ETP to estimate the ETP concentration and display the results in real-time.

In summary, the working procedure of the proposed ETP computing system includes the following steps.

Step 1:

In the beginning of the application of the system, the real-time and historical data of urban A²/O WWTPs need to be routinely collected and stored. The data may be collected by the online instrument for process variables which installed in WWTP and may be transferred to the "Data Management" module in the ETP computing system. When using in a real WWTP, the data may be transferred from hardware (online instrument) to software through PLC and the OPC sever on PC.

Step 2:

After step 1, the data that stored in ETP computing system need to be pre-processed to deal with missing and abnormal values. Moreover, for the characteristic of PLS algorithm, each variable need to be scaled to have zero mean and unit variance.

Step 3:

It is necessary to pre-process the data before they are processed by a soft-sensor. Thus in this disclosure, PLS technique is utilized to select the secondary variables for predicting the ETP values in the "ETP Online Estimate" module of the ETP computing system.

Step 4:

Extracting the pre-process data into the "Offline Training" module of the ETP computing system. In this step, data may be divided into training samples and testing samples. In addition, training and testing of the ETP computing model with different sets of data are performed to find the best ETP computing model and ensure its performance to online estimate ETP.

Step 5:

After step 4, the complete ETP computing model may be copied to the "ETP Online Estimate" module of the ETP computing system. Through PLC and the OPC server on PC, the system may collect the process data in real-time and feed them to the ETP computing model and predict the ETP values online.

Step 6:

Maintaining and updating the ETP computing model regularly through step 4 with historical data that stored in the system or the online instrument.

What is claimed is:

1. A method of measuring effluent total phosphorus (ETP) in a wastewater system, comprising the steps of:

collecting a first plurality of variables based on previously stored data by a hardware platform comprising a pretreatment tank, a first settler, an anaerobic tank, an anoxic tank, an oxic tank, a second settler, an effluent tank, and a computing system, the first plurality of variables comprising total suspended solid (TSS) values in an oxic tank, pH values through components of the hardware platform, temperatures through the components of the hardware platform, amounts of dissolved oxygen (DO) in the oxic tank, oxidation-reduction potentials (ORP) in the anaerobic tank, NH₄—N values, BOD values, COD values and $NO_3$—N values in the effluent tank, MLSS values in the anaerobic tank;

training the computing system using the first plurality of variables and a partial linear square (PLS) algorithm; further comprising:

using the first plurality of variables and the PLS algorithm comprises assigning an independent variable set as $X=[x_1, \ldots x_\alpha]$, wherein $\alpha$ is a number of the independent variables for n samples, assigning corresponding dependent variable vector as y, standardizing X and y using the PLS algorithm to generate a functional relation between x and y, and extracting v and u from matrixes derived from standardization of X and y such as to carry information of each of the matrixes and have a maximum degree of the functional relation, wherein the PLS algorithm is used to build a linear model by decomposing X and y into bilinear terms:

$$X = VP^T + E = \sum_{i=1}^{\alpha} v_i p_i^T + E, \quad (1)$$

$$y = UQ^T + F = \sum_{i=1}^{\alpha} u_i q_i^T + F, \quad (2)$$

Wherein:

V and U are a score matrix of X and y, respectively,
P and Q are a loading matrix of X and y, respectively,
E and F are a residual matrix of X and y block, respectively, $i=1, 2, \ldots, \alpha$, and $v_i$, $p_i$, $u_i$ and $q_i$ are corresponding vectors of V, P, U and Q;

calculating component $v_i$ and $u_i$ using:

$$u_i = b_i v_i, \quad (3)$$

$$b_i = u_i^T v_i / v_i^T v_i, \quad (4)$$

wherein $b_i$ is a regression coefficient, a vector of the regression coefficient is $b=[b_1, b_2, \ldots b_\alpha]^T$, and $\alpha$ is a number of independent variables; and selecting a termination condition of the PLS algorithm using:

$$R_{select} = \frac{\|b_{select}\|}{\|b\|}, \quad (5)$$

wherein $b_{select}$ is the vector of the regression coefficients of the selected variables, $\|\bullet\|$ is norm operation, and $R_{select}$ is set as 0.85;

selectively measuring, by the hardware platform, a second plurality of variables consisting of a TSS value in the pre-treatment tank, a pH value in the pre-treatment tank, a temperature in the pre-treatment tank, an amount of DO in the pre-treatment tank, and an ORP in the pre-treatment tank;

estimating the total phosphorus in the effluent tank based on the collected second plurality of variables using the trained computing system; and render the estimates available online.

\* \* \* \* \*